United States Patent
Backus et al.

(10) Patent No.: US 10,231,829 B2
(45) Date of Patent: Mar. 19, 2019

(54) LEAFLET STITCHING BACKER

(71) Applicant: BOSTON SCIENTIFIC SCIMED, INC., Maple Grove, MN (US)

(72) Inventors: Andrew J. H. Backus, Santa Cruz, CA (US); Anh Thu Pham, San Jose, CA (US)

(73) Assignee: BOSTON SCIENTIFIC SCIMED INC., Maple Grove, MN (US)

( * ) Notice: Subject to any disclaimer, the term of this patent is extended or adjusted under 35 U.S.C. 154(b) by 0 days.

(21) Appl. No.: 15/496,600

(22) Filed: Apr. 25, 2017

(65) Prior Publication Data
US 2017/0319335 A1 Nov. 9, 2017

Related U.S. Application Data

(60) Provisional application No. 62/331,646, filed on May 4, 2016.

(51) Int. Cl.
*A61F 2/24* (2006.01)

(52) U.S. Cl.
CPC ............ *A61F 2/2412* (2013.01); *A61F 2/243* (2013.01); *A61F 2/2418* (2013.01); *A61F 2/2436* (2013.01); *A61F 2220/0075* (2013.01); *A61F 2220/0091* (2013.01); *A61F 2250/0069* (2013.01)

(58) Field of Classification Search
CPC .............................. A61F 2/2412; A61F 2/2418
See application file for complete search history.

(56) References Cited

U.S. PATENT DOCUMENTS

| | | | |
|---|---|---|---|
| 8,709,077 B2 | 4/2014 | Schreck | |
| 8,894,702 B2 | 11/2014 | Quadri et al. | |
| 8,945,209 B2 | 2/2015 | Bonyuet et al. | |
| 9,114,008 B2 | 8/2015 | Benichou et al. | |
| 9,132,006 B2 | 9/2015 | Spenser et al. | |
| 9,155,619 B2 | 10/2015 | Liu et al. | |
| 9,168,131 B2 | 10/2015 | Yohanan et al. | |
| 2004/0039436 A1* | 2/2004 | Spenser | A61F 2/2412 623/1.13 |

(Continued)

FOREIGN PATENT DOCUMENTS

| WO | 2009042196 A2 | 4/2009 |
|---|---|---|
| WO | 2010030859 A1 | 3/2010 |

(Continued)

OTHER PUBLICATIONS

International Search Report and Written Opinion dated Jul. 21, 2017 for International Application No. PCT/US2017/030972.

*Primary Examiner* — Suba Ganesan
(74) *Attorney, Agent, or Firm* — Seager, Tufte & Wickhem, LLP.

(57) ABSTRACT

A replacement heart valve post and leaflet assembly may include at least a first post member including a body portion, a cantilevered leg portion, and a hinge portion configured to connect the body portion and the cantilevered leg portion and one or more leaflets. The cantilevered leg portion may comprise a longitudinally extending slot defined therein. At least a portion of a leaflet may extend through the slot. A backing element may be positioned over a portion of a leaflet such that the leaflet is secured between the cantilevered leg portion and the backing element.

19 Claims, 6 Drawing Sheets

(56) References Cited

U.S. PATENT DOCUMENTS

| | | |
|---|---|---|
| 2006/0259136 A1 | 11/2006 | Nguyen et al. |
| 2010/0185277 A1 | 7/2010 | Braido et al. |
| 2010/0262231 A1 | 10/2010 | Tuval et al. |
| 2011/0276128 A1 | 11/2011 | Cao et al. |
| 2012/0123529 A1 | 5/2012 | Levi et al. |
| 2013/0066419 A1 | 3/2013 | Gregg |
| 2013/0073037 A1 | 3/2013 | Gregg et al. |
| 2013/0150956 A1 | 6/2013 | Yohanan et al. |
| 2016/0030171 A1 | 2/2016 | Quijano et al. |
| 2016/0045307 A1 | 2/2016 | Yohanan et al. |
| 2016/0074161 A1 | 3/2016 | Bennett |

FOREIGN PATENT DOCUMENTS

| | | |
|---|---|---|
| WO | 2012162228 A1 | 11/2012 |
| WO | 2013013021 A2 | 1/2013 |
| WO | 2013013032 A2 | 1/2013 |
| WO | 2013086413 A1 | 6/2013 |
| WO | 2014145338 A1 | 9/2014 |
| WO | 2015126933 A1 | 8/2015 |

\* cited by examiner

LEAFLET STITCHING BACKER

CROSS-REFERENCE TO RELATED APPLICATIONS

This application claims priority to U.S. Provisional Application No. 62/331,646, filed May 4, 2016.

TECHNICAL FIELD

The present disclosure pertains to medical devices, and methods for manufacturing and/or using medical devices. More particularly, the present disclosure pertains to leaflet attachment mechanisms for a replacement heart valve.

BACKGROUND

A wide variety of intracorporeal medical devices have been developed for medical use, for example, intravascular use. Some of these devices include guidewires, catheters, medical device delivery systems (e.g., for stents, grafts, replacement valves, etc.), and the like. These devices are manufactured by any one of a variety of different manufacturing methods and may be used according to any one of a variety of methods. Of the known medical devices and methods, each has certain advantages and disadvantages. There is an ongoing need to provide alternative medical devices as well as alternative methods for manufacturing and using medical devices.

SUMMARY

This disclosure provides design, material, manufacturing method, and use alternatives for medical devices.

In a first example, a replacement heart valve post and leaflet assembly may comprise a first post member including a body portion, a cantilevered leg portion, and a hinge portion configured to connect the body portion and the cantilevered leg portion, wherein the cantilevered leg portion comprises a longitudinally extending slot defined therein. The replacement heart valve post and leaflet assembly may further comprise a first leaflet comprising at least a first sleeve, a second sleeve, and a body portion, wherein the first sleeve of the first leaflet extends through the slot of the cantilevered leg portion of the first post member and rests against an inner surface thereof, and a second leaflet comprising at least a first sleeve, a second sleeve, and a body portion, wherein the first sleeve of the second leaflet extends through the slot of the cantilevered leg portion of the first post member and rests against an inner surface thereof. The replacement heart valve post and leaflet assembly may further comprise a backing element positioned over the first sleeve of the first leaflet and the first sleeve of the second leaflet such that the first sleeves are positioned between the backing element and the cantilevered leg portion.

Alternatively or additionally to any of the examples above, in another example, the replacement heart valve post and leaflet assembly may further comprise a first plurality of apertures extending longitudinally along a first side of the backing element and a second plurality of apertures extending longitudinally along a second side of the backing element.

Alternatively or additionally to any of the examples above, in another example, the first sleeves of the first and second leaflets may extend laterally beyond a lateral edge of the cantilevered leg portion of the first post member.

Alternatively or additionally to any of the examples above, in another example, the backing element may extend laterally beyond at least one lateral edge of the cantilevered leg portion of the first post member.

Alternatively or additionally to any of the examples above, in another example, the backing element may be sutured to at least one of the first sleeves of the first and second leaflets.

Alternatively or additionally to any of the examples above, in another example, the backing element may be sutured to both of the first sleeves of the first and second leaflets.

Alternatively or additionally to any of the examples above, in another example, the first sleeves of the first and second leaflets may be free from direct fixation to the cantilevered leg portion of the first post member.

Alternatively or additionally to any of the examples above, in another example, the backing element may comprise a polymeric material.

Alternatively or additionally to any of the examples above, in another example, the backing element may comprises a metallic material.

Alternatively or additionally to any of the examples above, in another example, the replacement heart valve post and leaflet assembly may further comprise a hole formed in the backing element adjacent a top edge thereof.

Alternatively or additionally to any of the examples above, in another example, the backing element may be sutured to the cantilevered leg portion of the first post member through the hole.

Alternatively or additionally to any of the examples above, in another example, the body portion of the first post member may include a first hole extending laterally therethrough adjacent a proximal end of the body portion.

Alternatively or additionally to any of the examples above, in another example, the body portion of the first post member may include at least two holes extending from an outer surface to an inner surface thereof and adjacent a distal end of the body portion of the first post member.

Alternatively or additionally to any of the examples above, in another example, the backing element may be configured to prevent the first sleeves of the first and second leaflets from passing through the longitudinally extending slot of the first post member.

Alternatively or additionally to any of the examples above, in another example, the replacement heart valve post and leaflet assembly may further comprise a second post member, a third post member, and a third leaflet.

Another example replacement heart valve post and leaflet assembly may comprise a first post member including a body portion, a cantilevered leg portion, and a hinge portion configured to connect the body portion and the cantilevered leg portion, wherein the cantilevered leg portion comprises a longitudinally extending slot defined therein, a first leaflet comprising at least a first sleeve, a second sleeve, and a body portion, wherein the first sleeve of the first leaflet extends through the slot of the cantilevered leg portion of the first post member and rests against an inner surface thereof, a second leaflet comprising at least a first sleeve, a second sleeve, and a body portion, wherein the first sleeve of the second leaflet extends through the slot of the cantilevered leg portion of the first post member and rests against an inner surface thereof, and a backing element positioned over the first sleeve of the first leaflet and the first sleeve of the second leaflet such that the first sleeves are positioned between the backing element and the cantilevered leg portion of the first post member.

Alternatively or additionally to any of the examples above, in another example, the replacement heart valve post and leaflet assembly may further comprise a first plurality of apertures extending longitudinally along a first side of the backing element and a second plurality of apertures extending longitudinally along a second side of the backing element.

Alternatively or additionally to any of the examples above, in another example, the first sleeves of the first and second leaflets may extend laterally beyond a lateral edge of the cantilevered leg portion of the first post member.

Alternatively or additionally to any of the examples above, in another example, the backing element may extend laterally beyond at least one lateral edge of the cantilevered leg portion of the first post member.

Alternatively or additionally to any of the examples above, in another example, the backing element may be sutured to at least one of the first sleeves of the first and second leaflets.

Alternatively or additionally to any of the examples above, in another example, the backing element may be sutured to both of the first sleeves of the first and second leaflets.

Alternatively or additionally to any of the examples above, in another example, the first sleeves of the first and second leaflets may be free from direct fixation to the cantilevered leg portion of the first post member.

Alternatively or additionally to any of the examples above, in another example, the backing element may comprise a polymeric material.

Alternatively or additionally to any of the examples above, in another example, the backing element may comprise a metallic material.

Alternatively or additionally to any of the examples above, in another example, the replacement heart valve post and leaflet assembly may further comprise a hole formed in the backing element adjacent a top edge thereof.

Alternatively or additionally to any of the examples above, in another example, the backing element may be sutured to the cantilevered leg portion of the first post member through the hole.

Alternatively or additionally to any of the examples above, in another example, the backing element may be configured to prevent the first sleeves of the first and second leaflets from passing through the longitudinally extending slot of the first post member.

Another example replacement heart valve post and leaflet assembly may comprise a first post member including a body portion, a cantilevered leg portion, and a hinge portion configured to connect the body portion and the cantilevered leg portion, wherein the cantilevered leg portion comprises a longitudinally extending slot defined therein, a first leaflet comprising at least a first sleeve, a second sleeve, and a body portion, wherein the first sleeve of the first leaflet extends through the slot of the cantilevered leg portion of the first post member and rests against an inner surface thereof, a second leaflet comprising at least a first sleeve, a second sleeve, and a body portion, wherein the first sleeve of the second leaflet extends through the slot of the cantilevered leg portion of the first post member and rests against an inner surface thereof, and a backing element comprising a first plurality of apertures extending longitudinally along a first edge thereof and a second plurality of apertures extending longitudinally along a second edge thereof, the backing element positioned over the first sleeve of the first leaflet and the first sleeve of the second leaflet such that the first sleeves are positioned between the backing element and the cantilevered leg portion of the first post member and the backing element is configured to prevent the first sleeves of the first and second leaflets from passing through the longitudinally extending slot of the first post member.

Alternatively or additionally to any of the examples above, in another example, the first sleeves of the first and second leaflets may extend laterally beyond a lateral edge of the cantilevered leg portion of the first post member.

Alternatively or additionally to any of the examples above, in another example, the backing element may extend laterally beyond at least one lateral edge of the cantilevered leg portion of the first post member.

Alternatively or additionally to any of the examples above, in another example, the backing element may be sutured to at least one of the first sleeves of the first and second leaflets through at least one of the first or second plurality of apertures.

Alternatively or additionally to any of the examples above, in another example, the first sleeves of the first and second leaflets may be free from a direct coupling to the cantilevered leg portion of the first post member.

Alternatively or additionally to any of the examples above, in another example, the replacement heart valve post and leaflet assembly may further comprise a hole formed in the backing element adjacent a top edge thereof.

Alternatively or additionally to any of the examples above, in another example, the backing element may be sutured to the cantilevered leg portion of the first post member through the hole.

Another example replacement heart valve post and leaflet assembly may comprise a first post member including a body portion, a cantilevered leg portion, and a hinge portion configured to connect the body portion and the cantilevered leg portion, wherein the cantilevered leg portion comprises a longitudinally extending slot defined therein, a second post member including a body portion, a cantilevered leg portion, and a hinge portion configured to connect the body portion and the cantilevered leg portion, wherein the cantilevered leg portion comprises a longitudinally extending slot defined therein, a third post member including a body portion, a cantilevered leg portion, and a hinge portion configured to connect the body portion and the cantilevered leg portion, wherein the cantilevered leg portion comprises a longitudinally extending slot defined therein, a first leaflet comprising at least a first sleeve, a second sleeve, and a body portion, wherein the first sleeve of the first leaflet extends through the slot of the cantilevered leg portion of the first post member and rests against an inner surface thereof and the second sleeve of the first leaflet extends through the slot of the cantilevered leg portion of the second post member and rests against an inner surface thereof, a second leaflet comprising at least a first sleeve, a second sleeve, and a body portion, wherein the first sleeve of the second leaflet extends through the slot of the cantilevered leg portion of the first post member and rests against an inner surface thereof and the second sleeve of the second leaflet extends through the slot of the cantilevered leg portion of the third post member and rests against an inner surface thereof, a third leaflet comprising at least a first sleeve, a second sleeve, and a body portion, wherein the first sleeve of the third leaflet extends through the slot of the cantilevered leg portion of the second post member and rests against an inner surface thereof and the second sleeve of the third leaflet extends through the slot of the cantilevered leg portion of the third post member and rests against an inner surface thereof, a first backing element positioned over the first sleeve of the first leaflet and the first sleeve of the second leaflet such that the first sleeve of the first leaflet and the first sleeve of the second leaflet are positioned between the backing element and the cantilevered leg portion of the first post member, a second backing element positioned over the second sleeve of the first leaflet and the first sleeve of the third leaflet such that the second sleeve of the first leaflet and the first sleeve of the third leaflet are positioned between the backing element and the cantilevered leg portion of the second post member, and a third backing element positioned over the second sleeve of the second leaflet and the second sleeve of the third leaflet such that the second sleeve of the second leaflet and the second sleeve of the third leaflet are positioned between the backing element and the cantilevered leg portion of the third post member.

The above summary of some embodiments, aspects, and/or examples is not intended to describe each disclosed embodiment or every implementation of the present disclosure. The Figures, and Detailed Description, which follow, more particularly exemplify these embodiments.

BRIEF DESCRIPTION OF THE DRAWINGS

The disclosure may be more completely understood in consideration of the following detailed description of various embodiments in connection with the accompanying drawings, in which.

Figure 1:
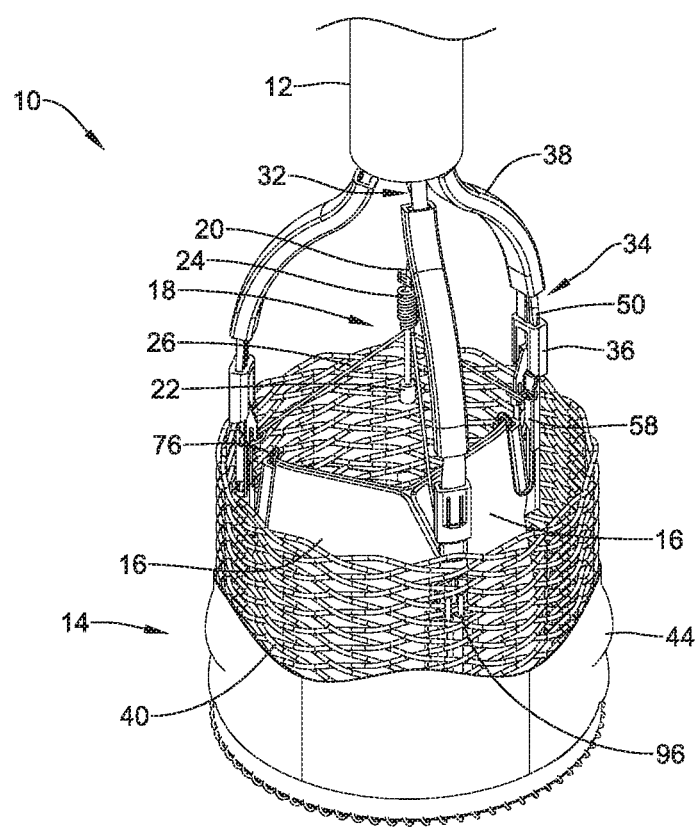
FIG. 1 is a perspective view of a portion of an example implant in a deployed configuration.

While aspects of the disclosure are amenable to various modifications and alternative forms, specifics thereof have been shown by way of example in the drawings and will be described in detail. It should be understood, however, that the intention is not to limit aspects of the disclosure to the particular embodiments described. On the contrary, the intention is to cover all modifications, equivalents, and alternatives falling within the spirit and scope of the disclosure.

DETAILED DESCRIPTION

The following description should be read with reference to the drawings, which are not necessarily to scale, wherein like reference numerals indicate like elements throughout the several views. The detailed description and drawings are intended to illustrate but not limit the claimed invention. Those skilled in the art will recognize that the various elements described and/or shown may be arranged in various combinations and configurations without departing from the scope of the disclosure. The detailed description and drawings illustrate example embodiments of the claimed invention.

For the following defined terms, these definitions shall be applied, unless a different definition is given in the claims or elsewhere in this specification.

All numeric values are herein assumed to be modified by the term "about," whether or not explicitly indicated. The term "about", in the context of numeric values, generally refers to a range of numbers that one of skill in the art would consider equivalent to the recited value (i.e., having the same function or result). In many instances, the term "about" may include numbers that are rounded to the nearest significant figure. Other uses of the term "about" (i.e., in a context other than numeric values) may be assumed to have their ordinary and customary definition(s), as understood from and consistent with the context of the specification, unless otherwise specified.

The recitation of numerical ranges by endpoints includes all numbers within that range, including the endpoints (e.g. 1 to 5 includes 1, 1.5, 2, 2.75, 3, 3.80, 4, and 5).

Although some suitable dimensions, ranges and/or values pertaining to various components, features and/or specifications are disclosed, one of skill in the art, incited by the present disclosure, would understand desired dimensions, ranges and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

Relative terms such as "proximal", "distal", "advance", "retract", variants thereof, and the like, may be generally considered with respect to the positioning, direction, and/or operation of various elements relative to a user/operator/manipulator of the device, wherein "proximal" and "retract" indicate or refer to closer to or toward the user and "distal" and "advance" indicate or refer to farther from or away from the user.

It is noted that references in the specification to "an embodiment", "some embodiments", "other embodiments", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it would be within the knowledge of one skilled in the art to effect such feature, structure, or characteristic in connection with other embodiments, whether or not explicitly described, unless clearly stated to the contrary. That is, the various individual elements described below, even if not explicitly shown in a particular combination, are nevertheless contemplated as being combinable or arrangable with each other to form other additional embodiments or to complement and/or enrich the described embodiment(s), as would be understood by one of ordinary skill in the art.

For the purpose of clarity, certain identifying numerical nomenclature (e.g., first, second, third, fourth, etc.) may be used throughout the description and/or claims to name and/or differentiate between various described and/or claimed features. It is to be understood that the numerical nomenclature is not intended to be limiting and is exemplary only. In some embodiments, alterations of and deviations from previously-used numerical nomenclature may be made in the interest of brevity and clarity. That is, a feature identified as a "first" element may later be referred to as a "second" element, a "third" element, etc. or may be omitted entirely, and/or a different feature may be referred to as the "first" element. The meaning and/or designation in each instance will be apparent to the skilled practitioner.

Diseases and/or medical conditions that impact the cardiovascular system are prevalent in the United States and throughout the world. Traditionally, treatment of the cardiovascular system was often conducted by directly accessing the impacted part of the system. For example, treatment of a blockage in one or more of the coronary arteries was traditionally treated using coronary artery bypass surgery. As can be readily appreciated, such therapies are rather invasive to the patient and require significant recovery times and/or treatments. More recently, less invasive therapies have been developed, for example, where a blocked coronary artery could be accessed and treated via a percutaneous catheter (e.g., angioplasty). Such therapies have gained wide acceptance among patients and clinicians.

Some relatively common medical conditions may include or be the result of inefficiency, ineffectiveness, or complete failure of one or more of the valves within the heart. For example, failure of the aortic valve can have a serious effect on a human and could lead to serious health condition and/or death if not dealt with. Treatment of defective heart valves poses other challenges in that the treatment often requires the repair or outright replacement of the defective valve. Such therapies may be highly invasive to the patient. Disclosed herein are medical devices that may be used for delivering a medical device to a portion of the cardiovascular system in order to diagnose, treat, and/or repair the system. At least some of the medical devices disclosed herein may be used to deliver and implant a replacement heart valve (e.g., a replacement aortic valve). In addition, the devices disclosed herein may deliver the replacement heart valve percutaneously and, thus, may be much less invasive to the patient. The devices disclosed herein may also provide a number of additional desirable features and benefits as described in more detail below.

FIG. 1 is a perspective view of a portion of an example medical implant system 10. It should be noted that some features of the medical implant system 10 are either not shown, or are shown schematically, in FIG. 1 for simplicity. Additional details regarding some of the components of the medical implant system 10 may be provided in other figures in greater detail. A medical implant system 10 may be used to deliver and/or deploy a variety of medical devices to a number of locations within the anatomy. In at least some embodiments, the medical implant system 10 may be a replacement heart valve system (e.g., a replacement aortic valve system) that can be used for percutaneous delivery of a replacement heart valve. This, however, is not intended to be limiting as the medical implant system 10 may also be used for other interventions including mitral valve replacement, valve repair, valvuloplasty, and the like, or other similar interventions.

The medical implant system 10 may generally be described as a catheter system that includes a delivery system 12 and a medical implant 14 (i.e., a valve replacement implant, for example) which may be coupled to the delivery system 12 and disposed within a lumen of the delivery system 12 during delivery of the medical implant 14. In some embodiments, a handle or actuator may be disposed at a proximal end of the delivery system 12. In general, the handle may be configured to manipulate the position of the delivery system 12, as well as aid in the deployment of the medical implant 14.

In use, the medical implant system 10 may be advanced percutaneously through the vasculature to a position adjacent to an area of interest. For example, the medical implant system 10 may be advanced through the vasculature and across the aortic arch to a position adjacent to a defective aortic valve (or other heart valve). During delivery, the medical implant 14 may be generally disposed in an elongated and low profile "delivery" configuration within the delivery system 12. Once positioned, the delivery system 12 may be retracted to expose the medical implant 14. The medical implant 14 may be actuated in order to radially expand the medical implant 14 into a generally shortened and larger profile "deployed" configuration suitable for implantation within the anatomy (as shown in FIG. 1, for example). When the medical implant 14 is suitably deployed within the anatomy, the delivery system 12 can be removed from the vasculature, leaving the medical implant 14 in place in a "released" configuration to function as, for example, a suitable replacement for the native aortic valve. In at least some interventions, the medical implant 14 may be deployed within the native valve (e.g., the native valve is left in place and not excised). Alternatively, the native valve may be removed and the medical implant 14 may be deployed in its place as a replacement.

In some embodiments, the delivery system 12 may include one or more lumens extending therethrough. For example, in some embodiments, the delivery system 12 may include a first lumen, a second lumen, a third lumen, and a fourth lumen. In general, the one or more lumens extend along an entire length of the delivery system 12. Other embodiments are contemplated, however, where one or more of the one or more lumens extend along only a portion of the length of the delivery system 12. For example, in some embodiments, the fourth lumen may stop just short of a distal end of the delivery system 12 and/or be filled in at its distal end to effectively end the fourth lumen proximal of the distal end of the delivery system 12.

Disposed within a first lumen of the delivery system 12 may be at least one actuator member, such as an actuator member 50 for example, which may be used to actuate (i.e., expand and/or elongate) the medical implant 14 between a delivery configuration and a deployed configuration. In some cases, the actuator member(s) 50 may herein be referred to, or used interchangeably with, the term "actuator element". In other words, the medical implant system 10 may include at least one actuator member 50. In some embodiments, the at least one actuator member 50 may include two actuator members 50, three actuator members 50, four actuator members 50, or another suitable or desired number of actuator members 50. For the purpose of illustration only, the medical implant system 10 and/or the medical implant 14 is shown with three actuator members 50.

In at least some embodiments, the first lumen may be lined with a low friction liner (e.g., a FEP liner). Disposed within a second lumen may be a pin release mandrel 20, which is explained in more detail herein. In at least some embodiments, the second lumen may be lined with a hypotube liner. A third lumen may be a guidewire lumen and in some embodiments, the third lumen may also be lined with a hypotube liner. In some embodiments, a fourth lumen may be used to house a non-stretch wire or other reinforcing member. The form of the non-stretch wire or other reinforcing member may vary. In some embodiments, the non-stretch wire may take the form of a stainless steel braid. The non-stretch wire may optionally include a pair of longitudinally-extending aramid and/or para aramid strands (for example, KEVLAR®) disposed on opposite sides of the braid. In general, rather than being "disposed within" the fourth lumen, the non-stretch wire may be embedded within the fourth lumen. In addition, the non-stretch wire may extend to a position adjacent to a distal end region but not fully to the distal end of the delivery system 12. For example, a short distal segment of the fourth lumen may be filled in with polymer material adjacent to the distal end of the delivery system 12.

The delivery system 12 may also include a guidewire tube extension that extends distally from the distal end region. In some embodiments, a nose cone may be attached to the guidewire tube extension. In some embodiments, the nose cone generally is designed to have an atraumatic shape. In some embodiments, the nose cone may also include a ridge or ledge that is configured to abut the distal tip of the delivery system 12 during delivery of the medical implant 14.

FIG. 1 illustrates some selected components of the medical implant system 10 and/or the medical implant 14. For example, here it can be seen that the medical implant 14 may include a plurality of valve leaflets 16 (e.g., bovine pericardial) which may be secured to a tubular anchor member or braid 40 that is reversibly actuatable between a "delivery" configuration and a "deployed" configuration. In some embodiments, the anchor member or braid 40 may be substantially cylindrical in shape or configuration. Some suitable but non-limiting materials for the anchor member or braid 40, for example metallic materials or polymeric materials, may be described below. In some embodiments, the medical implant 14 may include a plurality of locking mechanisms configured to secure the anchor member or braid 40 in the "deployed" configuration. In some embodiments, the at least one actuator member 50 may be configured to engage with the plurality of locking mechanisms and actuate the anchor member or braid 40 between the "delivery" configuration and the "deployed" configuration. In some embodiments, one actuator member 50 may correspond to, engage with, and/or actuate one locking mechanism. In some embodiments, one actuator member 50 may correspond to, engage with, and/or actuate more than one locking mechanism. Other configurations are also contemplated.

While a plurality of actuator members 50 and/or corresponding locking mechanisms may be included in a medical implant 14, for clarity and brevity, much of the following discussion will be limited to a single instance of these elements. The skilled person will readily recognize that the features and operation of the examples discussed below may apply equally to and across all instances of the plurality of locking mechanisms and/or the plurality of actuator members 50. Some suitable but non-limiting materials for the plurality of locking mechanisms and/or the plurality of actuator members 50, for example metallic materials or polymeric materials, may be described below.

In some embodiments, the plurality of locking mechanisms may each comprise an axially movable post member 76, for example at the commissure portions of the valve leaflets 16 (post member 76 may sometimes be referred to as a "commissure post"), and a buckle member 58 fixedly attached to the anchor member or braid 40. In other words, in at least some embodiments, a medical implant 14 may include a plurality of post members 76 and a corresponding plurality of buckle members 58. Other configurations and correspondences are also contemplated. In some embodiments, the post member 76 may engage the buckle member 58 in the "deployed" configuration. In some embodiments, the post member 76 may be axially or longitudinally spaced apart from the buckle member 58 in the "delivery" configuration. Some suitable but non-limiting materials for the post member 76 and/or the buckle member 58, for example metallic materials or polymeric materials, may be described below.

In some embodiments, a distal end 86 of the axially movable post member 76 may be secured and/or attached (i.e., fixedly attached, movably attached, removably attached, etc.) to a distal portion of the anchor member or braid 40, such as by a suture, a tether, adhesives, or other suitable element. In some embodiments, the post member 76 may be axially or longitudinally movable relative to the anchor member or braid 40 and/or the buckle member 58 may be fixedly attached to the anchor member or braid 40. Other embodiments are contemplated where the buckle member 58 may be movably or removably attached to the anchor member or braid 40. In some embodiments, the post member 76 may be fixedly attached to the anchor member or braid 40 and the buckle member 58 may be fixedly attached to the anchor member or braid 40. In some embodiments, one of the post member 76 and the buckle member 58 may be fixedly attached to the anchor member or braid 40 and the other may be movably or removably attached to the anchor member or braid 40. In some embodiments, the post member 76 may be movably or removably attached to the anchor member or braid 40 and the buckle member 58 may be movably or removably attached to the anchor member or braid 40. In some embodiments, the post member 76 may be secured or attached (i.e., fixedly attached, movably attached, removably attached, etc.) to a distal end of the anchor member or braid 40. In some embodiments, the buckle member 58 may be fixed or attached to a proximal portion of the anchor member or braid 40. In some embodiments, the buckle member 58 may be fixed or attached at or to a proximal end of the anchor member or braid 40.

In some embodiments, the medical implant 14 may include one or more of the plurality of valve leaflets 16 secured to the anchor member or braid 40 at, adjacent to, and/or using (at least in part) individual, corresponding post members 76, as will be described in more detail below. The valve leaflets 16 may also be secured to a base, or the distal end, of the anchor member or braid 40. Positioned adjacent to (e.g., aligned with) the plurality of post members 76 is a corresponding plurality of buckle members 58. In the illustrated examples, one buckle member 58 is attached to the anchor member or braid 40 adjacent to each of the three post members 76. Accordingly, the anchor member or braid 40 has a total of three buckle members 58 and three post members 76 attached thereto. Similarly, one actuator member 50 may be operatively associated with each post member 76 and buckle member 58, for a total of three actuator members 50 in the illustrated examples. Other embodiments are contemplated where fewer or more buckle members 58, post members 76, and actuator members 50 may be utilized. In some embodiments, a seal 44 may be disposed about the anchor member or braid 40 and, as the term suggests, may help to seal the medical implant 14 within and/or against a target site or area of interest upon deployment.

In some embodiments, attachment between the medical implant 14 and the delivery system 12 may be effected through the use of a coupler 32. In some embodiments, the coupler 32 may generally include a cylindrical base (not shown) that may be disposed about and/or attached to the delivery system 12. Projecting distally from the base is a plurality of fingers 34 (e.g., two, three, four, etc.) that are each configured to engage with the medical implant 14 at a proximal end of one of the buckle members 58. A collar 36 may be disposed about the fingers 34 of the coupler 32 to further assist in holding together the fingers 34 and the buckle members 58, as will be described in more detail below. A guide 38 may be disposed over each of the fingers 34 proximal of the collar 36 and may serve to keep the fingers 34 of the coupler 32 associated with the plurality of actuator members 50 extending adjacent to (and axially slidable relative to) the fingers 34 of the coupler 32. Finally, a pin release assembly 18 may be a linking structure that keeps post members 76, buckle members 58, and actuator members 50 associated with one another. In some embodiments, the pin release assembly 18 may include a plurality of individual pin members 26 that may be joined together via a coiled connection 24 and held to a pin release mandrel 20 with a ferrule 22. Some suitable but non-limiting materials for the coupler 32, the plurality of fingers 34, the collar 36, the guide 38, the pin release assembly 18, the plurality of individual pin members 26, the pin release mandrel 20 and/or the ferrule 22, for example metallic materials or polymeric materials, may be described below.

During delivery, the medical implant 14 may be secured at the distal end of the delivery system 12 by virtue of the association of the fingers 34 of the coupler 32 being coupled with a projecting proximal end of the buckle member 58 (and being held in place with the collar 36 disposed over the connection) and by virtue of the pin members 26 securing together the plurality of actuator members 50 and the post members 76, as will be described below. When the medical implant 14 is advanced to the target site or area of interest, the delivery system 12 may be withdrawn or retracted to expose the medical implant 14 (or the medical implant 14 may be advanced distally relative to the delivery system 12). Then, the plurality of actuator members 50 can be used to axially shorten and/or radially expand and "lock" the medical implant 14 and/or the anchor member or braid 40 from the "delivery" configuration to an expanded or "deployed" configuration (as shown in FIG. 1, for example) by proximally retracting the plurality of actuator members 50 to pull the post members 76 into engagement with the buckle members 58. Finally, the pin members 26 can be removed, thereby uncoupling the plurality of actuator members 50 from the post members 76, which allows the plurality of actuator members 50 and the fingers 34 of the coupler 32 to be withdrawn from the medical implant 14 thereby deploying the medical implant 14 (and/or the anchor member or braid 40) at the target site or area of interest in a "released" configuration. In other words, one difference between the "deployed" configuration and the "released" configuration is whether or not the pin members 26 are attached to the post members 76. In the "deployed" configuration, the pin members 26 are still attached to the post members 76, which thus permits the medical implant 14 (and/or the anchor member or braid 40) to be unlocked via distal advancement of the plurality of actuator members 50, as described further below, in order to reposition the medical implant 14, for example. In some embodiments, at least a portion of the plurality of valve leaflets 16 may axially or longitudinally overlap at least a portion of the buckle members 58 at a common position along a central longitudinal axis of the anchor member or braid 40, which in some embodiments may allow for a shorter overall length or height of the medical implant 14.

Figure 2:
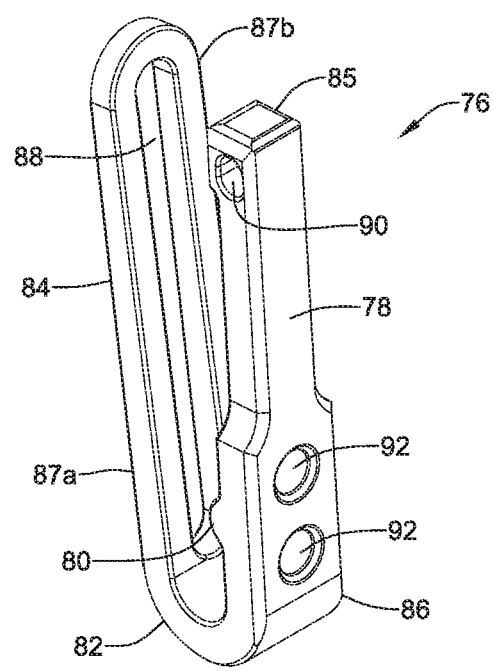
FIG. 2 is a perspective view of an example post member.

FIG. 2 illustrates a perspective view of an illustrative commissure post 76 to which the leaflets 16 may be secured. In some embodiments, the post member 76 may include a proximal end 85 and a distal end 86. In some embodiments, the post member 76 may include a body portion 78. The body portion 78 may include a protrusion 80 configured to engage bucket 58, or another portion of the actuator members 50. In some embodiments, the post member 76 may include a hole 90 extending laterally therethrough. The hole 90 may be configured to receive pin member 26, although this is not required. The post member 76 may further include one or more holes 92 for suturing 96 (see, for example, FIG. 1) the post member 76 to the braid 40.

In some embodiments, the post member 76 may include a cantilevered leg 84 connected by a flexible hinge portion 82 at the distal end 86. In some embodiments, the cantilevered leg 84 may extend proximally from the hinge portion 82 and/or the distal end 86 to a free end of the cantilevered leg 84 disposed radially inward from the body portion 78 (relative to the anchor member or braid 40). In some embodiments, the free end may be disposed proximal of the proximal end 85. The cantilevered leg 84 may include a slot 88 or aperture configured to receive one or more leaflets therethrough.

In some embodiments, the hinge portion 82 may have and/or include a radius of curvature. For example, in some embodiments, the radius of curvature may be between 0 and 3 millimeters (mm). In some embodiments, the radius of curvature may be an inner radius of curvature of between 0 and 3 millimeters (mm). In some embodiments, the radius of curvature may be an outer radius of curvature of between 0 and 3 millimeters (mm). Other configurations and radii of curvature are also contemplated. In some embodiments, the hinge portion 82 may be configured to dispose the body portion 78 and the cantilevered leg 84 at an acute angle relative to each other. In some embodiments, the acute angle may be between about 0 degrees and about 90 degrees, between about 3 degrees and about 60 degrees, between about 5 degrees and about 45 degrees, between about 8 degrees and about 30 degrees, between about 10 degrees and about 20 degrees, between about 12 degrees and about 16 degrees, about 14 degrees, or another suitable angle. In at least some embodiments, the hinge portion 82 flexibly attaches the cantilevered leg 84 to the body portion 78 of the post member 76. In some embodiments, at least part of the cantilevered leg 84 may longitudinally overlap the buckle member 58 along a central longitudinal axis of the anchor member or braid 40 in the "deployed" configuration.

In some embodiments, the cantilevered leg 84 may include a free end and a secured end, where the cantilevered leg 84 may be attached to the body portion 78 of the post member 76 at the secured end, which may connect directly to the hinge portion 82. In some embodiments, the free end of the cantilevered leg 84 may be unattached (i.e., not directly attached) to any other structure of the medical implant 14, except for the cantilevered leg 84 and/or the plurality of valve leaflets 16. In other words, in some embodiments, the free end may not be directly attached to any other structure or feature of the medical implant 14 (i.e., the buckle member 58, the anchor member or braid 40, etc.). In some embodiments, a distalmost end of the post member 76, which in at least some embodiments may be and/or include the hinge portion 82, may be coupled to the distal end of the anchor member or braid 40, such as, for example, by a fastening element such as a suture, filament, wire, or other suitable means. As such, when the post member 76 is pulled proximally to engage the buckle member 58, the distal end of the anchor member or braid 40 is also pulled proximally relative to the buckle member 58, thereby transitioning from the "delivery" configuration toward the "deployed" configuration.

In some embodiments, the body portion 78 may be unitary with and/or integrally formed with the latch portion 80, the hinge portion 82, the cantilevered leg 84, and/or the attachment section 88 as and/or from a single piece of material. In some embodiments, the post member 76 may be formed from a single piece of wire, flat stock, or other suitable material as discussed herein. In some embodiments, the post member 76 may be formed by further processing the single piece of wire, flat stock, or other suitable material, such as by machining, stamping, laser cutting, etc. Some suitable but non-limiting materials for the body portion 78, the hinge portion 82, and/or the cantilevered leg 84, for example metallic materials or polymeric materials, may be described below.

In at least some embodiments, one or more of the plurality of valve leaflets 16 may be attached to the cantilevered leg(s) 84. In some embodiments, attachment of the plurality of valve leaflets 16 to the cantilevered leg(s) 84 may provide flexibility and/or a reduction in stress between the plurality of valve leaflets 16 to the anchor member or braid 40. In some embodiments, the plurality of valve leaflets 16 may be secured directly to the cantilevered leg(s) 84. In some embodiments, the plurality of valve leaflets 16 may not be directly secured to the body portion 78 of the post member 76, but is instead coupled to the post member 76 via the cantilevered leg(s) 84. In some embodiments, the plurality of valve leaflets 16 may be wrapped around at least a portion of the cantilevered leg(s) 84. In some embodiments, a distalmost end of the plurality of valve leaflets 16 may be coupled to the distal end of the anchor member or braid 40. In some embodiments, the plurality of valve leaflets 16 may be coupled and/or secured (i.e., to the cantilevered leg 84, to the anchor member or braid 40, and/or back to themselves) using one or more sutures, threads, wires, filaments, or other suitable elements. In some embodiments, the plurality of valve leaflets 16 may be coupled and/or secured (i.e., to the cantilevered leg 84, to the anchor member or braid 40, and/or back to themselves) using an adhesive, a bonding agent, or other suitable securing means. In some embodiments, the plurality of valve leaflets 16 may be coupled and/or secured (i.e., to the cantilevered leg 84, to the anchor member or braid 40, and/or back to themselves) using a fabric, a textile, or other thin flexible material.

Figure 3:
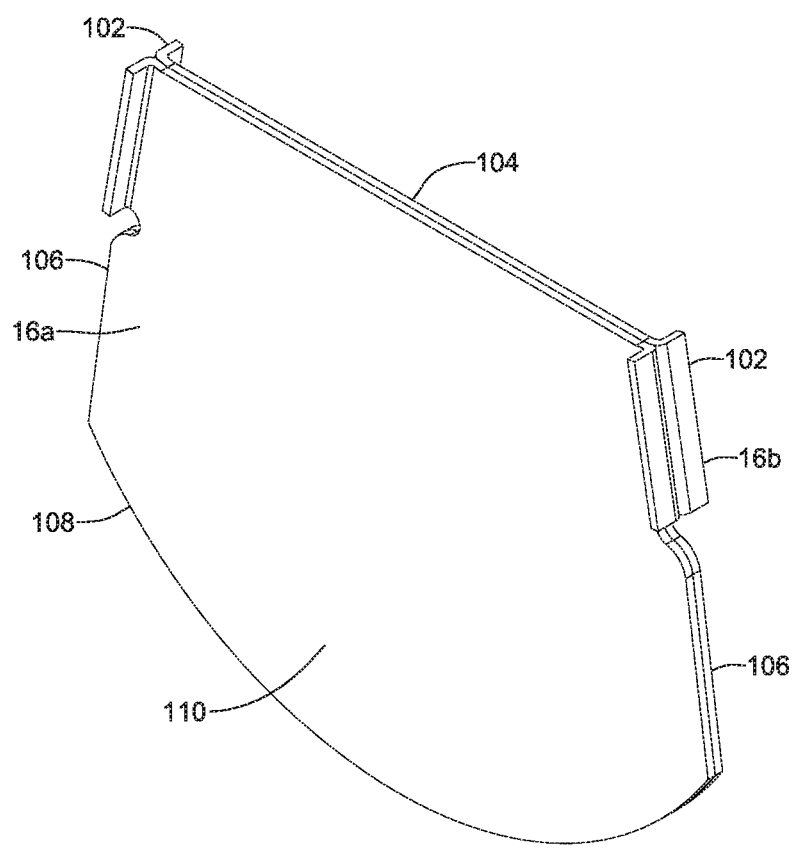
FIG. 3 is a perspective view of two illustrative leaflets.

FIG. 3 illustrates a pair of leaflets 16a, 16b (collectively 16) positioned side by side for attachment to post member 76. Each of the leaflets 16 may include a pair of sleeves 102, a free edge 104, two side edges 106, a bottom edge 108, and a "belly" or body region 110. For clarity, these features have only been identified on one of the leaflets 16 in FIG. 3. It is contemplated that the shape of the leaflets 16 may vary from that which is shown in FIG. 3. For example, the sleeves 102 may be longer, shorter, angled, etc. or the bottom edge 108 may have more curve, less curvature, etc. These are just examples.

The leaflets 16 may be secured to post assemblies 76 using a suturing process. The bottom edges of the valve leaflets 16 may be sutured to the lower edge of an adaptive seal and the adaptive seal may be lashed to the bottom-most crowns of the stent. In general, the overall process may include sewing together the leaflets 16 along their side edges 106, attaching the sleeves 102 to the posts 76, securing the posts 76 to the braid 40, and tacking down the tissue bellies 110 with temporary stitches to hold leaflets in the correct orientation and attaching the seal 44 to the leaflets 16 with equidistant whipstitches while the tissue is fixed to the frame. The temporary stitches are removed as the seal-leaflet stitches are completed.

Figure 4:
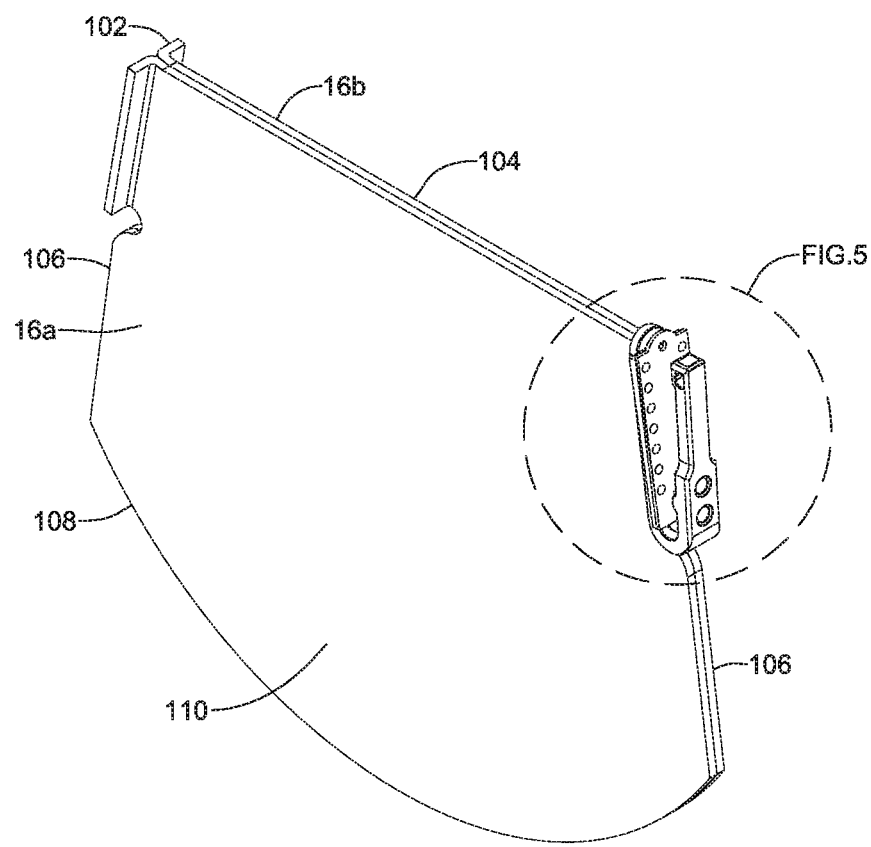
FIG. 4 is a perspective view of two illustrative leaflets engaged with an illustrative post member.
Figure 5:
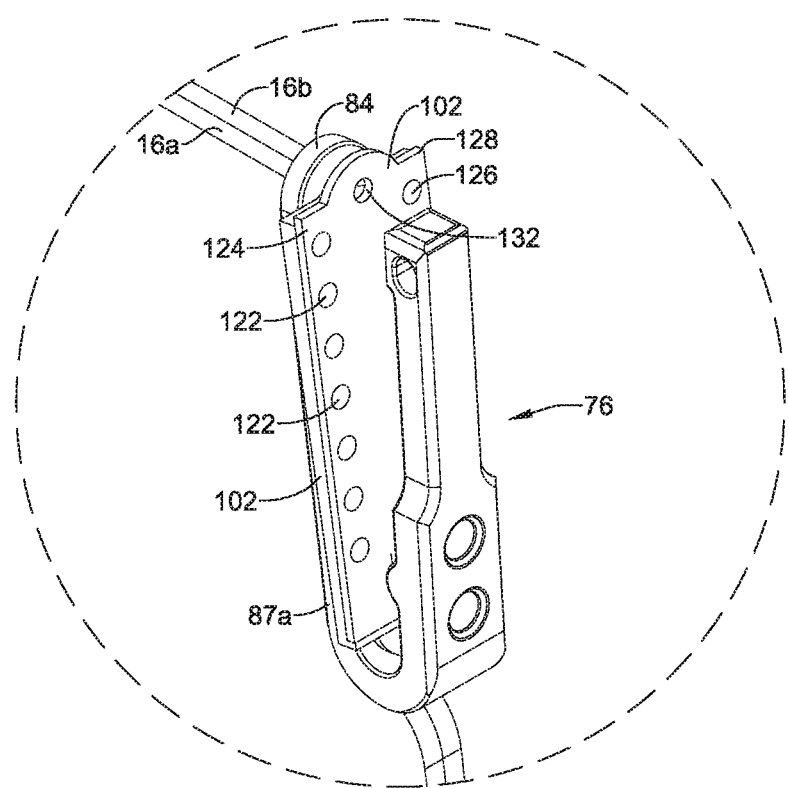
FIG. 5 is a close up perspective view of two illustrative leaflets engaged with an illustrative post member.
Figure 6:
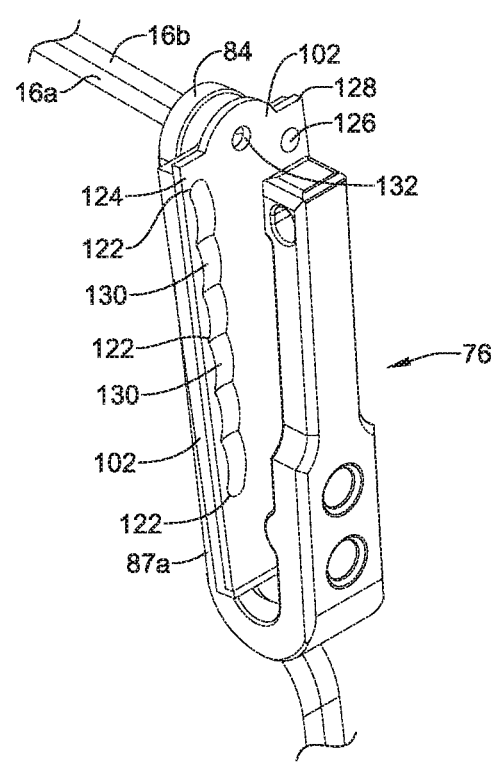
FIG. 6 is a close up perspective view of two illustrative leaflets engaged with an illustrative post member including suturing.

The attachment of the leaflets 16 to post member 76 will now be described in more detail with respect to FIGS. 4-6. To attach the leaflets 16 to the post 76, a sleeve 102 from two adjacent leaflets 16 may be advanced though the slot 88 in the cantilevered leg 84. The sleeves 102 may be folded over the cantilevered leg 84 such that sleeves 102 extend laterally beyond an edge 87a,b of the cantilevered leg 84 and a surface of the sleeve(s) rests against an inner surface of the cantilevered leg 84. The sleeves 102 may be positioned such that a first sleeve is oriented towards a first lateral edge 87a of the cantilevered leg 84 and a second sleeve is oriented towards a second lateral edge 87b, opposite the first lateral edge 87a, of the cantilevered leg. While the sleeves 102 are illustrated as extending only a short distance beyond an edge 87a,b of the cantilevered leg 84, it is contemplated that the sleeves 102 may be longer or shorter, as desired. For example, the sleeves 102 may have length that facilitates advancement through the slot 88 and/or alignment and are subsequently trimmed.

Once the sleeves 102 are advanced through the slot 88, a backing element 120 may be placed over the sleeves 102. The backing element 120 may be positioned between the body portion 78 and the sleeves 102 of the leaflets 16. In other words, the sleeves 102 may be secured between the cantilevered leg 84 and the backing element 120. The backing element 120 may be formed from a material which has sufficient rigidity to prevent the sleeves 102 from slipping back through the slot 88. In some instances, the backing element 120 may be formed from a polyether ether ketone (PEEK), although this is just an example. Other illustrative materials may include, but are not limited to, acrylics, polyamides, polycarbonates, polyethylene (PE), high density polyethylene (HDPE), ultra-high molecular weight polyethylene UHMWPE), polyformaldehyde (for example an acetal such as but not limited to DELRIN®), polypropylene, polytetrafluoroethylene (PTFE) (for example, TEFLON™), fluorinated ethylene propylene (FEP), polyurethane, polycarbonate-urethane (PCU), silicones, etc. It is contemplated that any biocompatible thermoplastic, or other polymer, may also be used. Some additional suitable but non-limiting materials for the backing element 120, for example, metallic materials, ceramic materials, polymeric materials, or composites thereof, may be described below.

The backing element 120 may include a first plurality of apertures 122 extending along a first side 124 and a second plurality of apertures 126 extending along a second side 128. While not explicitly shown, the second plurality of apertures 126 may be a mirror image of the first plurality of apertures 122. However, this is not required. In some instances, the first plurality of apertures 122 may include a different number of apertures from the second plurality of apertures 126. The first plurality of apertures 122 may be configured to facilitate suturing of the backing element 120 to a sleeve 102 of a first leaflet 16a. For example, as shown in FIG. 6, the backing element 120 may be sutured to the sleeve 102 using, for example, a running stitch 130. In some embodiments, the stitching pattern may be performed twice such that there are no gaps between adjacent stitches, as shown in FIG. 6. It is contemplated that a single pass of a running stitch pattern may result in adjacent stitches being alternating between opposite sides of the backing element 120 and/or sleeve 102. Other stitches may also be used to suture the backing element 120 to the sleeve 102, as desired. While the apertures 122 are described as a plurality of apertures, it is contemplated that the backing element may include any number of apertures 122 desired, such as one, two, three, four, or more. In some instances, the apertures 122 may not be present. The second plurality of apertures 126 may be configured to facilitate suturing of the backing element 120 to a sleeve 102 of a second leaflet 16b. While the apertures 126 are described as a plurality of apertures, it is contemplated that the backing element may include any number of apertures 126 desired, such as one, two, three, four, or more. In some instances, the apertures 126 may not be present.

The first and second sides 124, 128 of the backing element 120 may extend beyond the edges 87 of the cantilevered leg 84. This may allow the backing element 120 to be sutured to the sleeves 102 of the leaflets 16 without suturing the backing element 120 and/or the leaflets 16 to the post 76. This is just an example. In some instances, the backing element 120 and/or the leaflets 16 may be sutured to the post 76. It is contemplated that the backing element 120 and/or the sleeves 102 may be trimmed to reduce their size once the backing element 120 has been sutured to the sleeves 102. In some embodiments, the backing element 120 may include an aperture 132 configured to be positioned adjacent to the free end of the cantilevered leg 74. This may allow the backing element 120 to be sutured to the cantilevered leg 74, although this is not required. In some embodiments, the backing element 120 may have a generally rectangular shape with a curved protrusion extending therefrom. However, the backing element 120 may take any shape desired. The curved protrusion may have a similar profile (e.g. size and/or shape) to the free end of the cantilevered leg 74. The aperture 132 may be positioned within and/or adjacent to the curved protrusion.

It is contemplated that if three leaflets 16 are used, three posts 76 may also be used to secure the leaflets to each other and to the braid 40. Each post 76 may secure a sleeve 102 from a leaflet 16 and another sleeve 102 of an adjacent leaflet 16.

The materials that can be used for the various components of the medical implant system 10 (and/or other systems disclosed herein) and the various elements thereof disclosed herein may include those commonly associated with medical devices. For simplicity purposes, the following discussion makes reference to the delivery system 12 and/or the medical implant 14. However, this is not intended to limit the devices and methods described herein, as the discussion may be applied to other elements, members, components, or devices disclosed herein, such as, but not limited to, the anchor member or braid 40, the actuator member 50, the post member 76, the buckle member 58, the pin member 26, and/or elements or components thereof.

In some embodiments, the delivery system 12 and/or the medical implant 14, and/or components thereof, may be made from a metal, metal alloy, polymer (some examples of which are disclosed below), a metal-polymer composite, ceramics, combinations thereof, and the like, or other suitable material. Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

As alluded to herein, within the family of commercially available nickel-titanium or nitinol alloys, is a category designated "linear elastic" or "non-super-elastic" which, although may be similar in chemistry to conventional shape memory and super elastic varieties, may exhibit distinct and useful mechanical properties. Linear elastic and/or non-super-elastic nitinol may be distinguished from super elastic nitinol in that the linear elastic and/or non-super-elastic nitinol does not display a substantial "superelastic plateau" or "flag region" in its stress/strain curve like super elastic nitinol does. Instead, in the linear elastic and/or non-super-elastic nitinol, as recoverable strain increases, the stress continues to increase in a substantially linear, or a somewhat, but not necessarily entirely linear relationship until plastic deformation begins or at least in a relationship that is more linear than the super elastic plateau and/or flag region that may be seen with super elastic nitinol. Thus, for the purposes of this disclosure linear elastic and/or non-super-elastic nitinol may also be termed "substantially" linear elastic and/or non-super-elastic nitinol.

In some cases, linear elastic and/or non-super-elastic nitinol may also be distinguishable from super elastic nitinol in that linear elastic and/or non-super-elastic nitinol may accept up to about 2-5% strain while remaining substantially elastic (e.g., before plastically deforming) whereas super elastic nitinol may accept up to about 8% strain before plastically deforming. Both of these materials can be distinguished from other linear elastic materials such as stainless steel (that can also be distinguished based on its composition), which may accept only about 0.2 to 0.44 percent strain before plastically deforming.

In some embodiments, the linear elastic and/or non-super-elastic nickel-titanium alloy is an alloy that does not show any martensite/austenite phase changes that are detectable by differential scanning calorimetry (DSC) and dynamic metal thermal analysis (DMTA) analysis over a large temperature range. For example, in some embodiments, there may be no martensite/austenite phase changes detectable by DSC and DMTA analysis in the range of about −60 degrees Celsius (° C.) to about 120° C. in the linear elastic and/or non-super-elastic nickel-titanium alloy. The mechanical bending properties of such material may therefore be generally inert to the effect of temperature over this very broad range of temperature. In some embodiments, the mechanical bending properties of the linear elastic and/or non-super-elastic nickel-titanium alloy at ambient or room temperature are substantially the same as the mechanical properties at body temperature, for example, in that they do not display a super-elastic plateau and/or flag region. In other words, across a broad temperature range, the linear elastic and/or non-super-elastic nickel-titanium alloy maintains its linear elastic and/or non-super-elastic characteristics and/or properties.

In some embodiments, the linear elastic and/or non-super-elastic nickel-titanium alloy may be in the range of about 50 to about 60 weight percent nickel, with the remainder being essentially titanium. In some embodiments, the composition is in the range of about 54 to about 57 weight percent nickel. One example of a suitable nickel-titanium alloy is FHP-NT alloy commercially available from Furukawa Techno Material Co. of Kanagawa, Japan. Other suitable materials may include ULTANIUM™ (available from Neo-Metrics) and GUM METAL™ (available from Toyota). In some other embodiments, a superelastic alloy, for example a superelastic nitinol can be used to achieve desired properties.

In at least some embodiments, portions or all of the delivery system 12 and/or the medical implant 14, and/or components thereof, may also be doped with, made of, or otherwise include a radiopaque material. Radiopaque materials are understood to be materials capable of producing a relatively bright image on a fluoroscopy screen or another imaging technique during a medical procedure. This relatively bright image aids the user of the medical implant system 10 in determining its location. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of the medical implant system 10 to achieve the same result.

In some embodiments, a degree of Magnetic Resonance Imaging (Mill) compatibility is imparted into the medical implant system 10. For example, the delivery system 12 and/or the medical implant 14, and/or components or portions thereof, may be made of a material that does not substantially distort the image and create substantial artifacts (i.e., gaps in the image). Certain ferromagnetic materials, for example, may not be suitable because they may create artifacts in an Mill image. The delivery system 12 and/or the medical implant 14, or portions thereof, may also be made from a material that the MRI machine can image. Some materials that exhibit these characteristics include, for example, tungsten, cobalt-chromium-molybdenum alloys (e.g., UNS: R30003 such as ELGILOY®, PHYNOX®, and the like), nickel-cobalt-chromium-molybdenum alloys (e.g., UNS: R30035 such as MP35-N® and the like), nitinol, and the like, and others.

A sheath or covering (not shown) may be disposed over portions or all of the delivery system 12 that may define a generally smooth outer surface for the medical implant system 10. In other embodiments, however, such a sheath or covering may be absent from a portion of all of the medical implant system 10, such that the delivery system 12 may form an outer surface. The sheath may be made from a polymer or other suitable material. Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like. In some embodiments the sheath can be blended with a liquid crystal polymer (LCP). For example, the mixture can contain up to about 6 percent LCP.

In some embodiments, an exterior surface of the medical implant system 10 (including, for example, the exterior surface of the delivery system 12) may be sandblasted, beadblasted, sodium bicarbonate-blasted, electropolished, etc. In these as well as in some other embodiments, a coating, for example a lubricious, a hydrophilic, a protective, or other type of coating may be applied over portions or all of the sheath, or in embodiments without a sheath over portion of the delivery system 12, or other portions of the medical implant system 10. Alternatively, the sheath may comprise a lubricious, hydrophilic, protective, or other type of coating. Hydrophobic coatings such as fluoropolymers provide a dry lubricity which improves device handling and device exchanges. Lubricious coatings improve steerability and improve lesion crossing capability. Suitable lubricious polymers are well known in the art and may include silicone and the like, hydrophilic polymers such as high-density polyethylene (HDPE), polytetrafluoroethylene (PTFE), polyarylene oxides, polyvinylpyrolidones, polyvinylalcohols, hydroxy alkyl cellulosics, algins, saccharides, caprolactones, and the like, and mixtures and combinations thereof. Hydrophilic polymers may be blended among themselves or with formulated amounts of water insoluble compounds (including some polymers) to yield coatings with suitable lubricity, bonding, and solubility.

The coating and/or sheath may be formed, for example, by coating, extrusion, co-extrusion, interrupted layer co-extrusion (ILC), or fusing several segments end-to-end. The layer may have a uniform stiffness or a gradual reduction in stiffness from the proximal end to the distal end thereof. The gradual reduction in stiffness may be continuous as by ILC or may be stepped as by fusing together separate extruded tubular segments. The outer layer may be impregnated with a radiopaque filler material to facilitate radiographic visualization. Those skilled in the art will recognize that these materials can vary widely without deviating from the scope of the present invention.

It should be understood that this disclosure is, in many respects, only illustrative. Changes may be made in details, particularly in matters of shape, size, and arrangement of steps without exceeding the scope of the invention. This may include, to the extent that it is appropriate, the use of any of the features of one example embodiment being used in other embodiments. The invention's scope is, of course, defined in the language in which the appended claims are expressed.

What is claimed is:

1. A replacement heart valve post and leaflet assembly, the assembly comprising:
   a first post member including a body portion, a cantilevered leg portion, and a hinge portion configured to connect the body portion and the cantilevered leg portion, wherein the cantilevered leg portion comprises a longitudinally extending slot defined therein;
   a first leaflet comprising at least a first sleeve, a second sleeve, and a body portion, wherein the first sleeve of the first leaflet extends through the slot of the cantilevered leg portion of the first post member and rests against an inner surface thereof;

a second leaflet comprising at least a first sleeve, a second sleeve, and a body portion, wherein the first sleeve of the second leaflet extends through the slot of the cantilevered leg portion of the first post member and rests against an inner surface thereof; and a backing element positioned over the first sleeve of the first leaflet and the first sleeve of the second leaflet such that the first sleeves are positioned between the backing element and the cantilevered leg portion of the first post member, further comprising a first plurality of apertures extending longitudinally along a first side of the backing element and a second plurality of apertures extending longitudinally along a second side of the backing element.

2. The replacement heart valve post and leaflet assembly of claim 1, wherein the first sleeves of the first and second leaflets extend laterally beyond a lateral edge of the cantilevered leg portion of the first post member.

3. The replacement heart valve post and leaflet assembly of claim 1, wherein the backing element extends laterally beyond at least one lateral edge of the cantilevered leg portion of the first post member.

4. The replacement heart valve post and leaflet assembly of claim 1, wherein the backing element is sutured to at least one of the first sleeves of the first and second leaflets.

5. The replacement heart valve post and leaflet assembly of claim 1, wherein the backing element is sutured to both of the first sleeves of the first and second leaflets.

6. The replacement heart valve post and leaflet assembly of claim 1, wherein the first sleeves of the first and second leaflets are free from direct fixation to the cantilevered leg portion of the first post member.

7. The replacement heart valve post and leaflet assembly claim 1, wherein the backing element comprises a polymeric material.

8. The replacement heart valve post and leaflet assembly claim 1, wherein the backing element comprises a metallic material.

9. The replacement heart valve post and leaflet assembly of claim 1, further comprising a hole formed in the backing element adjacent a top edge thereof.

10. The replacement heart valve post and leaflet assembly of claim 9, wherein the backing element is sutured to the cantilevered leg portion of the first post member through the hole.

11. The replacement heart valve post and leaflet assembly of claim 1, wherein the backing element is configured to prevent the first sleeves of the first and second leaflets from passing through the longitudinally extending slot of the first post member.

12. A replacement heart valve post and leaflet assembly, the assembly comprising:

a first post member including a body portion, a cantilevered leg portion, and a hinge portion configured to connect the body portion and the cantilevered leg portion, wherein the cantilevered leg portion comprises a longitudinally extending slot defined therein;

a first leaflet comprising at least a first sleeve, a second sleeve, and a body portion, wherein the first sleeve of the first leaflet extends through the slot of the cantilevered leg portion of the first post member and rests against an inner surface thereof;

a second leaflet comprising at least a first sleeve, a second sleeve, and a body portion, wherein the first sleeve of the second leaflet extends through the slot of the cantilevered leg portion of the first post member and rests against an inner surface thereof; and a backing element comprising a first plurality of apertures extending longitudinally along a first edge thereof and a second plurality of apertures extending longitudinally along a second edge thereof, the backing element positioned over the first sleeve of the first leaflet and the first sleeve of the second leaflet such that the first sleeves are positioned between the backing element and the cantilevered leg portion of the first post member and the backing element is configured to prevent the first sleeves of the first and second leaflets from passing through the longitudinally extending slot of the first post member.

13. The replacement heart valve post and leaflet assembly of claim 12, wherein the first sleeves of the first and second leaflets extend laterally beyond a lateral edge of the cantilevered leg portion of the first post member.

14. The replacement heart valve post and leaflet assembly of claim 12, wherein the backing element extends laterally beyond at least one lateral edge of the cantilevered leg portion of the first post member.

15. The replacement heart valve post and leaflet assembly of claim 12, wherein the backing element is sutured to at least one of the first sleeves of the first and second leaflets through at least one of the first or second plurality of apertures.

16. The replacement heart valve post and leaflet assembly of claim 12, wherein the first sleeves of the first and second leaflets are free from a direct coupling to the cantilevered leg portion of the first post member.

17. The replacement heart valve post and leaflet assembly of claim 12, further comprising a hole formed in the backing element adjacent a top edge thereof.

18. The replacement heart valve post and leaflet assembly of claim 17, wherein the backing element is sutured to the cantilevered leg portion of the first post member through the hole.

19. A replacement heart valve post and leaflet assembly, the assembly comprising:

a first post member including a body portion, a cantilevered leg portion, and a hinge portion configured to connect the body portion and the cantilevered leg portion, wherein the cantilevered leg portion comprises a longitudinally extending slot defined therein;

a second post member including a body portion, a cantilevered leg portion, and a hinge portion configured to connect the body portion and the cantilevered leg portion, wherein the cantilevered leg portion comprises a longitudinally extending slot defined therein;

a third post member including a body portion, a cantilevered leg portion, and a hinge portion configured to connect the body portion and the cantilevered leg portion, wherein the cantilevered leg portion comprises a longitudinally extending slot defined therein;

a first leaflet comprising at least a first sleeve, a second sleeve, and a body portion, wherein the first sleeve of the first leaflet extends through the slot of the cantilevered leg portion of the first post member and rests against an inner surface thereof and the second sleeve of the first leaflet extends through the slot of the cantilevered leg portion of the second post member and rests against an inner surface thereof;

a second leaflet comprising at least a first sleeve, a second sleeve, and a body portion, wherein the first sleeve of the second leaflet extends through the slot of the cantilevered leg portion of the first post member and rests against an inner surface thereof and the second sleeve of the second leaflet extends through the slot of the cantilevered leg portion of the third post member and rests against an inner surface thereof;
a third leaflet comprising at least a first sleeve, a second sleeve, and a body portion, wherein the first sleeve of the third leaflet extends through the slot of the cantilevered leg portion of the second post member and rests against an inner surface thereof and the second sleeve of the third leaflet extends through the slot of the cantilevered leg portion of the third post member and rests against an inner surface thereof;
a first backing element positioned over the first sleeve of the first leaflet and the first sleeve of the second leaflet such that the first sleeve of the first leaflet and the first sleeve of the second leaflet are positioned between the backing element and the cantilevered leg portion of the first post member;
a second backing element positioned over the second sleeve of the first leaflet and the first sleeve of the third leaflet such that the second sleeve of the first leaflet and the first sleeve of the third leaflet are positioned between the backing element and the cantilevered leg portion of the second post member; and
a third backing element positioned over the second sleeve of the second leaflet and the second sleeve of the third leaflet such that the second sleeve of the second leaflet and the second sleeve of the third leaflet are positioned between the backing element and the cantilevered leg portion of the third post member,
further comprising a first plurality of apertures extending longitudinally along a first side of the backing elements and a second plurality of apertures extending longitudinally along a second side of the backing elements.

* * * * *